US007442189B2

(12) United States Patent
Curutcharry

(10) Patent No.: US 7,442,189 B2
(45) Date of Patent: Oct. 28, 2008

(54) RE-FORMING DEVICE IN PARTICULAR FOR MIXING SUBSTANCES IN THE MEDICAL FIELD

(75) Inventor: Jean Curutcharry, Guethary (FR)

(73) Assignee: Technoflex (SA), Bidart (FR)

( * ) Notice: Subject to any disclaimer, the term of this patent is extended or adjusted under 35 U.S.C. 154(b) by 1053 days.

(21) Appl. No.: 10/433,455

(22) PCT Filed: Dec. 6, 2001

(86) PCT No.: PCT/FR01/03853

§ 371 (c)(1),
(2), (4) Date: Jun. 3, 2003

(87) PCT Pub. No.: WO02/45649

PCT Pub. Date: Jun. 13, 2002

(65) Prior Publication Data

US 2004/0015148 A1 Jan. 22, 2004

(30) Foreign Application Priority Data

Dec. 6, 2000 (FR) .................................. 00 15823

(51) Int. Cl.
*A61M 5/32* (2006.01)
*A61B 19/00* (2006.01)

(52) U.S. Cl. ....................... 604/416; 604/403; 604/414; 604/415

(58) Field of Classification Search ......... 604/403–416, 604/88, 4.01–6.16; 128/DIG. 24; 206/21; 220/265; 137/601, 614.04
See application file for complete search history.

(56) References Cited

U.S. PATENT DOCUMENTS

| | | | | |
|---|---|---|---|---|
| 5,653,698 | A | 8/1997 | Niedospial et al. | |
| 6,113,583 | A * | 9/2000 | Fowles et al. | 604/403 |

* cited by examiner

*Primary Examiner*—Tatyana Zalukaeva
*Assistant Examiner*—Phil Wiest
(74) *Attorney, Agent, or Firm*—Young & Thompson

(57) ABSTRACT

A re-forming device in particular for mixing substances in the medical field, includes a hollow needle pointed at its two tips and fixed on a support defining two coaxial sleeves enclosing each end of the needle and designed to receive, one, the plug opening of a vial, the other, the hub of an injection tube of a flexible bag, so as to communicate, by perforating the plug and hub, the vial and the flexible bag via the needle. The sleeve, on the side of the flexible bag, is dimensioned and designed to be engaged on the hub in a first stable position wherein the device is secured to the bag without the needle being in contact with the hub and the sleeve is mounted sliding on the hub so as to pass, through simple depression of the device on the hub, from the first position into a second position, corresponding to the perforation of the hub by the needle.

8 Claims, 1 Drawing Sheet

Fig. 1
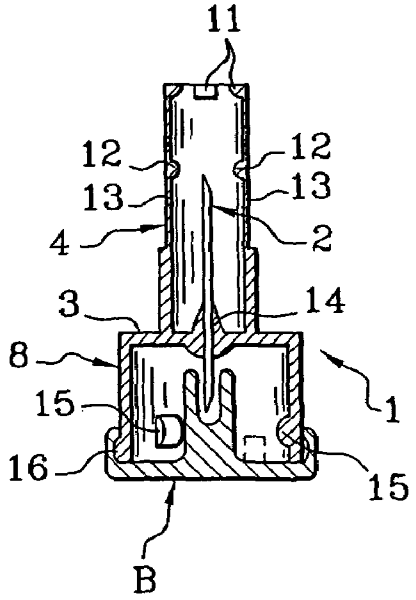
Fig. 2
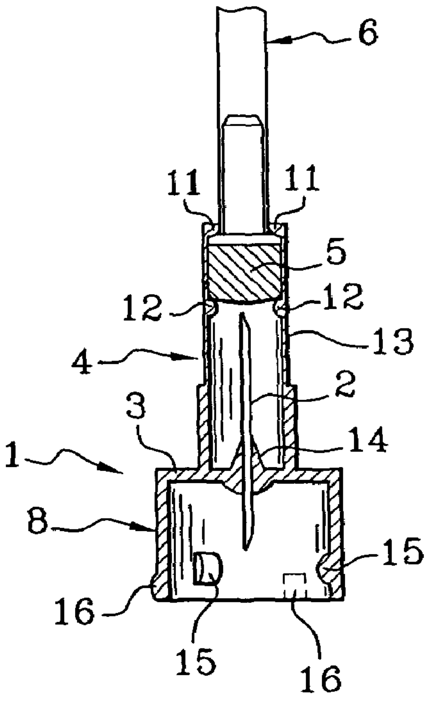
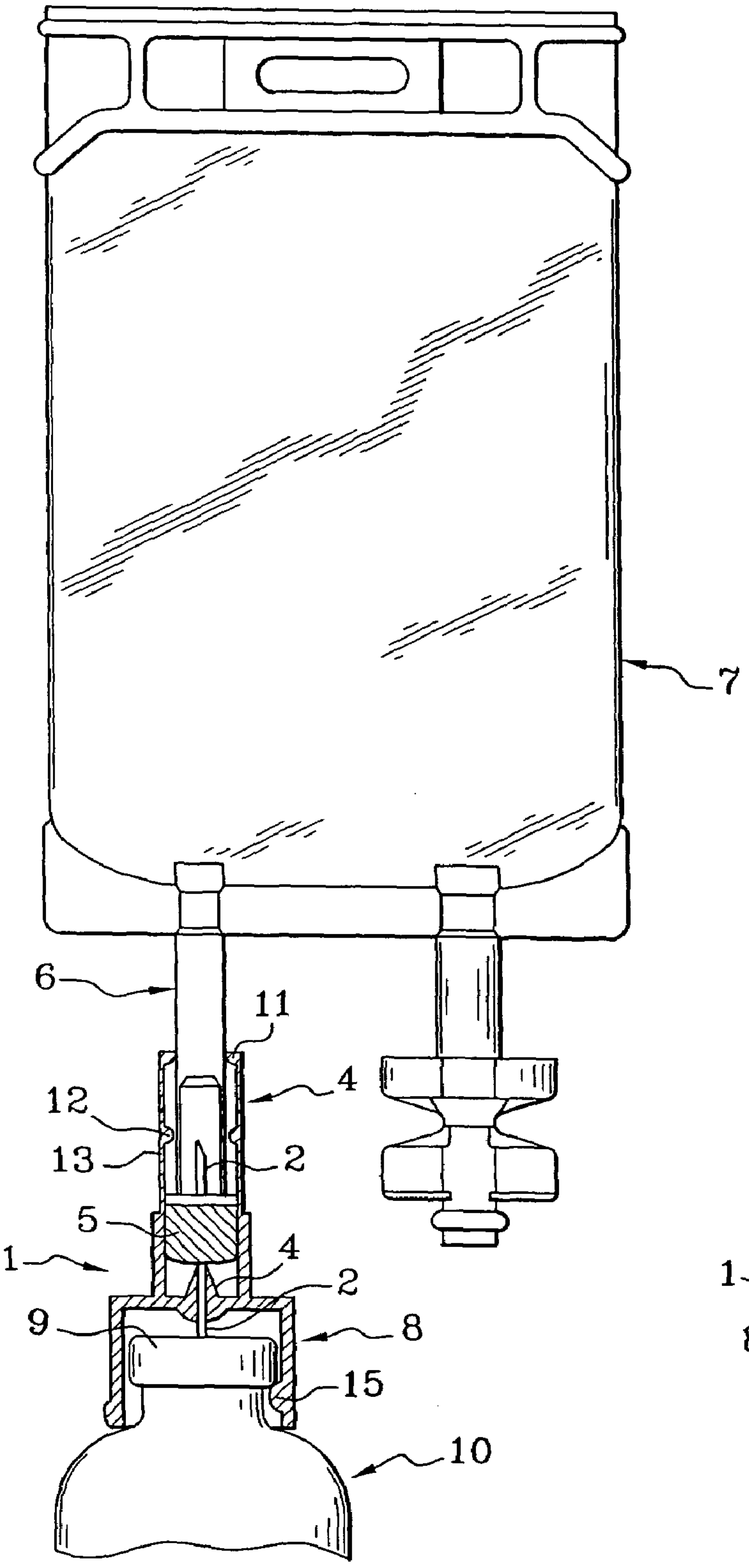
Fig. 3

RE-FORMING DEVICE IN PARTICULAR FOR MIXING SUBSTANCES IN THE MEDICAL FIELD

BACKGROUND OF THE INVENTION

The present invention relates to the mixing of one substance with another substance, particularly in the medical field, so as for example to reconstitute a medication by means of a diluant.

More precisely, the invention relates to the device, commonly called a reconstitution device, adapted to carry out such a mixing.

Various medications that must be interjected intravenously into a patient must first be mixed with a diluant which can for example be a dextrose solution, a saline solution or even water.

A good number of these medications are stored in glass vials in the form of powder or in the liquid condition.

At the time of their administration, these medications must be mixed with a diluant contained in a flexible bag provided for this purpose with an injection tube comprising a tip of a material such as rubber for example, adapted to be pierced by a needle, the passage formed by this latter closing itself upon retraction of the needle.

Conventionally, the communication between the vial of medication and the flexible bag is ensured with the help of a reconstitution device constituted by a hollow needle pointed at both its ends and projecting into two open cylindrical sockets disposed head to tail and shaped to receive, one of them, the mouth of the vial with its rubber plug for example and, the other, the tip of the injection tubing of the flexible bag.

At the time of use of the medication, the reconstitution device is separated from its sterile packaging, the needle, on the vial side of the device is sunk through the plug, then the other needle is also introduced through the tip of the flexible bag, the communication between this latter and the vial being thus ensured by way of the reconstitution device.

Such a system has the drawback of requiring separate storing of the flexible bags, the vials and the reconstitution devices.

SUMMARY OF THE INVENTION

The object of the present invention is to simplify this system and to render it more economical by associating the reconstitution device and the flexible bag upon production of this latter by pre-positioning said device, and by packaging the device plus bag assembly in a single sterile package.

To this end, the invention has for its object a reconstitution device particularly for mixing substances in the medical field, of the type comprising a hollow needle, pointed at both its ends and fixed on a support defining two coaxial sockets enclosing each end of the needle and adapted to receive, one of them, the plugged mouth of a vial and, the other, the tip of an injection tube of a flexible bag, such that by a perforation of said plug and tip, to place the vial and the flexible bag into communication via said needle, characterized in that said socket, on the flexible bag side, is so dimensioned and arranged as to engage on the tip in a first stable position in which the device is secured to the bag without the needle being in contact with the tip and in that said socket is slidably mounted on the tip so as to pass, by a simple sinking of the device into the tip, from said first position to a second stable position corresponding to the piercing of the tip by the needle.

It is thus possible to store particularly in a sterile package, the flexible bag-reconstitution device assembly which forms a unitary assembly ready to be used because the reconstitution device is already in place, without however the needle being inserted in the tip of the bag whose content can thus remain totally isolated from the outside. A single assembly is thus to be managed, stored and handled.

At the time of use of the bag, it suffices to remove the sterile packaging if there is one, engage the plug of a vial in the socket of the device so as to pierce the plug, then to sink the reconstitution device-vial assembly on the tip until this latter is pierced and its complete engagement in the receiving socket takes place, such that the reconstitution device will be operational.

The vial surface of the device can be conventional and comprise a conventional socket for the reception of what is also a conventional vial.

Preferably, the reconstitution device is provided with positioning and retaining means, at least in the first of the mentioned positions, for the tip socket on the tip of the injection tube of the flexible bag.

The invention also has for its object the assembly constituted by a flexible bag provided with at least one injection tube with a pre-positioned tip in said first retaining position in the socket in question of the reconstitution device.

The device of the invention thus has substantial advantages, particularly as to ease of management and use.

BRIEF DESCRIPTION OF THE DRAWINGS

Other characteristics and advantages will become apparent from the description which follows, of an embodiment of the device of the invention, which description is given solely by way of example and with respect to the accompanying drawing, in which:

FIG. 1 is an axial cross-sectional view of a reconstitution device according to the invention;

FIG. 2 shows the device of FIG. 1 in place in a ready position on the end of an injection tube of a flexible bag and, FIG. 3 shows the device of FIG. 1 in the second or operational position.

DETAILED DESCRIPTION OF THE PREFERRED EMBODIMENTS

The reconstitution device shown at 1 in FIG. 1 comprises a hollow needle 2 passing through a circular support 3 prolonged toward each pointed end of the needle, by a cylindrical socket.

One of the sockets (4) is adapted to receive (FIGS. 2 and 3) the tip 5 of an injection tube 6 of a flexible bag 7.

The other socket 8, disposed head to tail relative to the socket 4, has a greater diameter to receive the mouth provided with a plug 9 (FIG. 3) of a vial 10 of medication for example. The socket 8 has an internal diameter adapted to the vial 10 and is closed during non-use by a plug B for safety. The length of the socket 8 is slightly greater than that of the projecting portion of the needle 2.

The socket 4 is very substantially longer than the projecting portion of the needle 2 so as to receive (FIG. 2) all of the tip 5 in a region at a distance from the pointed end of said needle.

The internal diameter of the socket 4 corresponds to the external diameter of the tip 5 whose wall is of resilient material.

The tip 5 is of conventional structure of a material such as latex permitting its piercing by the needle 2, the passage hole closing by itself after retraction of the needle, as is also true of the material of the plug 9.

At its inlet opening, the socket 4 is provided internally with a slight annular flange 11, discontinuous as shown, or not, provided that at a distance from this flange 11 corresponding to the length of the tip 5 are provided one or several small internal projections, for example two projections 12 diametrically opposed, shaped to the end of two tongues 13 cut out from the wall of the socket 4.

The device 1 is of one-piece construction and made for example by molding a suitable plastic material.

FIG. 2 shows the device 1 pre-positioned on the injection tube 6, in the ready position. The device 1 is located in its first stable position, the tip 5 having been engaged in the socket 4 forcefully to pop over, thanks to the resilience of the tip, the inlet flange 11, the tip 5 being introduced completely and being stopped in this first position by the two projections 12.

In this stable ready position, the point of the needle 2 is held at a distance from the tip 5 and the device 1 forms a body with the flexible bag 7. The assembly can thus be manipulated, packaged in a sterile flexible packaging, stored and managed as a single item.

During use of the bag 7, which is to say when it is desired to mix the content of the vial 10 with a dilution liquid, for example contained in the bag, the device 1 is first placed on the tubing 6 in the position of FIG. 2 (ready position). Then the vial 10 is introduced by its plug 9 into the socket 8 such that the plug is pierced. Finally, the assembly of device 1-vial 10 is pressed in the direction of the bag 7 so as to pierce the tip 5 by the needle.

At the beginning of this movement, it is necessary to overcome the slight resilient resistance of the projections 12 which retract to let the tip pass, then all of the tip 5 is pierced by the needle 2, and finally the tip comes into abutment in the second stable position of the device 1 against a cone 14 provided in the bottom of the socket 4.

The bag 7 and vial 10 are thus in communication via the needle 2 and the tube 6.

It is of course possible to provide this communication by first engaging the plug 9 of the vial 10 into the socket 8 to pierce the plug, then by engaging the assembly of the device 1-vial 10 on the tip 5 so as finally to piece the tip 5 and to bring the assembly into the position of FIG. 3.

The device of the invention has the advantage of permitting withdrawing the assembly of the device 1-vial 10 from the tip 5 after the reconstitution operation. Thus, the operator will have a bag 7 with which he can, via the tube 6, carry out an additional injection if necessary. According to another advantage, the separation between the bag 7 and the assembly 1-10 is desirable for optimum treatment of hospital waste.

Finally, the invention is clearly not limited to the embodiment shown and described above, but on the contrary covers all modifications, particularly to a means for positioning-blocking the tip 5 in its first position other than using flange 11 and projections 12. It is to be noted that the socket 8 could if desired be provided internally in the manner known with one or several projections, three for example, such as shown at 15 in the figures, so as resiliently to retain in the correct sunken position the plug 9 of the vial, and externally also in known manner, with one or several projections, three for example, such as shown at 16 to retain the plug B.

The invention claimed is:

1. A reconstitution device, comprising:

a one-piece support;

a hollow needle, pointed at both ends and fixed on said support, said support defining two coaxial sockets enclosing each end of said needle, a first one of said sockets being adapted to receive a plugged mouth of a vial and a second one of said sockets being adapted to receive a tip of an injection tube of a flexible bag, so that perforating a plug of a vial and a tip of an injection tube places a vial in communication with a flexible bag via said needle, said first one of said sockets including a continuous or discontinuous flange projecting inwardly adjacent an inlet opening of said first one of said sockets and at least one resiliently retractable projection within said first one of said sockets and spaced apart from said flange that together with said flange engage a tip of an injection tube in a first stable position in which said device is secured to a flexible bag without said needle being in contact with a tip of an injection tube, said first one of said sockets being slidably mounted on a tip of an injection tube so as to pass, by simple sinking of the device against a tip of an injection tube, from said first stable position to a second stable position, said needle piercing a tip of an injection tube in said second stable position.

2. The device according to claim 1, wherein said support is a molded plastic material.

3. The device according to claim 1, wherein said second one of said sockets comprises at least one inward projection that resiliently retains a plugged mouth of a vial.

4. The device according to claim 1, wherein said second one of said sockets comprises at least one outward projection for retaining an end plug.

5. An assembly comprising:

a flexible bag having at least one injection tube with a tip, said tip being pre-positioned between said flange and said retractable projection of the device according to claim 1.

6. The assembly according to claim 5, wherein a distance between said flange and said retractable projection is equal to a length of said tip.

7. A reconstitution device, comprising:

a one-piece support;

a hollow needle, pointed at both ends and fixed on said support, said support defining two coaxial sockets enclosing each end of said needle, a first one of said sockets including a flange projecting inwardly adjacent an inlet opening of said first one of said sockets and at least one resiliently retractable projection within said first one of said sockets and spaced apart from said flange, a tip of an injection tube connected to a flexible bag being between said flange and said retractable projection in a first position, a tip of an injection tube connected to a flexible bag being spaced apart from said flange and said retractable projection in a second position, said needle piercing a tip of an injection tube in said second position.

8. A reconstitution device, comprising:

a one-piece support;

a hollow needle, pointed at both ends and fixed on said support, said support defining two coaxial sockets enclosing each end of said needle, said first one of said sockets including means for positioning and blocking a tip of an injection tube connected to a flexible bag.

* * * * *